United States Patent [19]

Ayer et al.

[11] Patent Number: 4,610,686
[45] Date of Patent: Sep. 9, 1986

[54] CONTROLLED DELIVERY OF HALOPERIDOL BY AN OSMOTIC DELIVERY SYSTEM

[75] Inventors: Atul Ayer, Mountain View; Felix Theeuwes, Los Altos; Patrick S. L. Wong, Hayward, all of Calif.

[73] Assignee: ALZA Corporation, Palo Alto, Calif.

[21] Appl. No.: 547,789

[22] Filed: Nov. 2, 1983

[51] Int. Cl.⁴ .............................................. A61M 7/00
[52] U.S. Cl. .................................... 604/890; 604/891; 604/892; 604/893; 604/894; 604/895; 604/896
[58] Field of Search ............... 604/892, 890, 891, 893, 604/894, 895, 896

[56] References Cited

U.S. PATENT DOCUMENTS

| | | | |
|---|---|---|---|
| 3,845,770 | 11/1974 | Theeuwes et al. | 604/893 |
| 3,916,899 | 11/1975 | Theeuwes et al. | 604/893 |
| 4,008,719 | 2/1977 | Theeuwes et al. | 604/893 |
| 4,036,228 | 7/1977 | Theeuwes et al. | 604/893 |

Primary Examiner—John Kight
Assistant Examiner—M. L. Moore
Attorney, Agent, or Firm—Paul L. Sabatine; Edward L. Mandell; Steven F. Stone

[57] ABSTRACT

An osmotic system is disclosed for the delivery of haloperidol at a controlled rate over a prolonged period of time.

15 Claims, 7 Drawing Figures

CONTROLLED DELIVERY OF HALOPERIDOL BY AN OSMOTIC DELIVERY SYSTEM

FIELD OF THE INVENTION

This invention pertains to the controlled delivery of a therapeutically useful amount of haloperidol by an osmotic delivery system. The invention concerns also both a process for solubilizing haloperidol and an improved method for producing a therapeutic effect by administering the solubilized haloperidol.

BACKGROUND OF THE INVENTION

Haloperidol, also known as 4-[4-(-chlorophenyl)-4-hydroxy-1-piperidnyl]-1-(4-fluorophenyl)-1-butanone, is a tranquilizer drug indicated for the management of manifestation of psychotic disorders. Haloperidol is specifically indicated as an antipsychotic drug useful for the treatment of acute and chronic schizophrenia.

Presently, haloperidol is available as conventional tablets. These noncontrolled dosage tablets containing 0.5 mg to 2.0 mg of haloperidol are administered to patients of moderate symptomatology twice or thrice daily, and the same tablet containing 3.0 mg to 5.0 mg of haloperidol are administered to patients of severe symptomatology also twice or thrice daily.

The duration of drug delivery of these conventional dosage forms is almost instant, or at best a few hours. This short duration of drug delivery has at least two detrimental effects. The first is the need for frequent administration that leads to a failure of patient compliance with the dosage schedules. Accompanying this failure is not only the lack of administration effectiveness, but also a possible increase in unwanted side effects arising from patients increasing their dosage to compensate for prior omissions. The second detrimental effect is periodic interval administration almost inevitably leads to a peak level of drug surpassing the amount of drug needed at the time of administration, followed by a decline in the level of drug falling below the amount needed to achieve the desired therapeutic effect.

It is self-evident, in the light of the above discussion, a pressing and critical need exists for a delivery dosage form that can deliver haloperidol at a controlled rate and continuously over a prolonged period of time. The need exists for haloperidol as the prior art has not provided a controlled-delivery form for haloperidol, and because its physical and chemical properties do not lend themselves to controlled delivery forms. That is, haloperidol is light-sensitive, nonhygroscopic and practically insoluble in water, which properties are poorly suited for controlled delivery forms.

OBJECTS OF THE INVENTION

Accordingly, it is an immediate object of this invention to provide an osmotically controlled delivery form that contributes to the dispensing art by making available a dosage form that dispenses haloperidol at a controlled and continuous rate over a prolonged period of time.

Another object of the present invention is to provide an improvement in haloperidol therapy by making available an osmotic delivery system containing haloperidol in a solubilized form for its controlled and continuous delivery over time.

Another object of the present invention is to provide an osmotic delivery system for the controlled delivery of haloperidol with once-a-day dosing for its bioavailability and pharmacokinetic effects.

Yet another object of the invention is to provide an improved therapeutic method for administering haloperidol, which method comprises administering haloperidol at a controlled rate of release over a prolonged period of time to a needy patient.

Still yet another object of the invention is to provide an osmotic system comprising a compartment containing haloperidol maintained in a high solubility state for enhancing substantially complete delivery to a warm-blooded recipient.

These and other objects of the invention will become more apparent from a consideration of the accompanying detailed disclosure and the accompanying claims.

BRIEF DESCRIPTION OF THE DRAWINGS

In FIG. 4, the first 4 hours of release are measured in artificial gastric fluid, and the next 8 hours are measured in artificial intestinal fluid.

Figure 6:
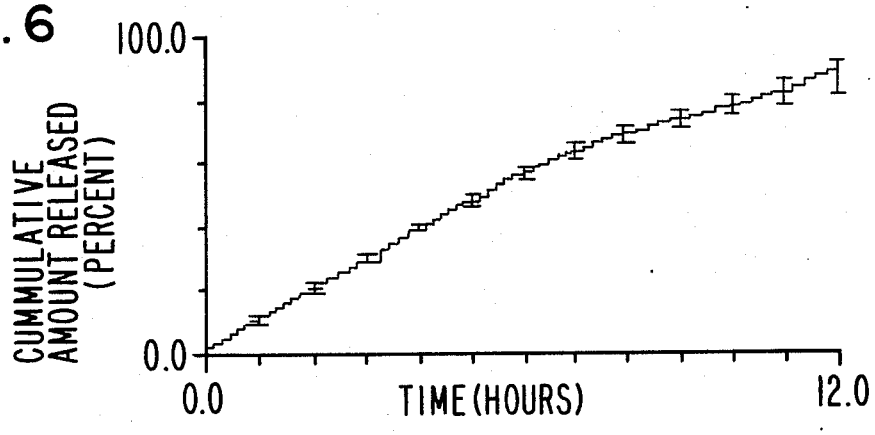

The cumulative rate of release is depicted in FIG. 6. In the Figure, the bars represent the maximum and minimum rate of release for 6 measurements at the time of measurement. In this example haloperidol and citric acid are present in a 1 to 100 ratio. The final osmotic device has a 0.36 mm passageway, the compartment weighed 214 mg and consisted of 0.94% haloperidol, 93.6% citric acid, 1.75% noncross-linked Povidone, 1.75% cross-linked Povidone and 2% magnesium stearate. The semipermeable wall weighed 14 mg.

Figure 7:
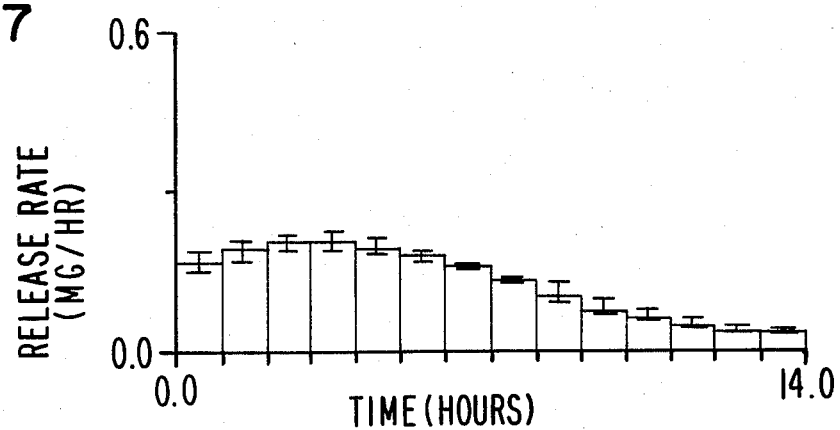

The release rate in mg/hr for haloperidol is illustrated in FIG. 7.

DETAILED DESCRIPTION OF THE DRAWINGS

This invention resides in the discovery that haloperidol can be administered from an osmotic delivery system over a prolonged period of time. Prior to this invention, haloperidol could not be delivered by an osmotic delivery device because it is practically insoluble in water exhibiting a solubility of less than 0.1 mg/ml, and because it exhibits a near zero osmotic pressure. Now, it has been unexpectedly found the useful drug haloperidol can be successfully delivered by an osmotic device by substantially increasing the solubility of haloperidol by blending haloperidol with a saturated or an unsaturated 2 carbon, 3 carbon, or 4 carbon dicarboxylic or tricarboxylic acid, and in an embodiment, a 2 carbon, 3 carbon or 4 carbon hydroxydicarboxylic, hydroxytricarboxylic or dihydroxydicarboxylic acids. Representative dicarboxylic and tricarboxylic acid includes a member selected from the group consisting essentially of citric acid, maleic acid, and maleic acid, dihydroxy succinic acid and mixtures thereof. In an embodiment, the invention further comprises succinic acid mixed with at least one member selected from the group consisting essentially of citric acid, maleic acid and malic acid. For example, haloperidol blended with citric acid becomes very soluble and exhibits a solubility $S_d$ of 165 mg/ml, citric acid exhibits a solubility $S_o$ in the presence of haloperidol of 555 mg/ml, and the total solubility, $S_t$, of haloperidol and citric acid of 720 mg/ml in aqueous solution. The equilibrium ratio, in one measurement, of citric acid/haloperidol for a mutually saturated solution was 3.4 to 1. The invention generically encompasses a citric acid to haloperidol ratio of 3 parts citric acid to 1 part haloperidol up to 100 parts of citric acid to 1 part haloperidol, usually the parts are in weight. In a presently preferred embodiment, the ratio of carboxylic acid to haloperidol is 3 parts carboxylic acid to 1 part haloperidol up to 100 parts of carboxylic acid to 1 part haloperidol, as for example the ratios of citric acid to haloperidol embrace 46 to 1, 20 to 1, 16 to 1, 12 to 1 and 8 to 1. The mutually saturated solution comprising haloperidol and citric acid exhibited an osmotic pressure of 150 atmospheres at the 3.4 ratio. Haloperidol blended with maleic acid exhibited an enhanced solubility of greater than 200 mg/ml in aqueous solution, and haloperidol blended with malic acid exhibited an enhanced solubility of greater than 250 mg/ml in a saturated haloperidol malic acid aqueous solution. The mutually generated properties of high solubility and high osmotic pressure leads to the manufacture of an osmotic device that can successfully deliver haloperidol at a controlled rate over a prolonged period of time.

The haloperidol is delivered by an osmotic device comprising a wall that surrounds and defines a compartment. The compartment contains both a dosage amount of haloperidol and the di- or tricarboxylic acid. The compartment optionally contains dispensing ingredients used for easy manufacture and controlled delivery.

The wall of the osmotic delivery device is formed of a semipermeable composition that does not adversely affect the haloperidol, the di- or tricarboxylic acid, or a biological host. The wall is formed of a semipermeable composition that is permeable to the passage of an external fluid, such as water and biological fluids, and it is essentially impermeable to the passage of haloperidol, the di- and tricarboxylic acid, and other ingredients in the compartment. The selectively permeable polymers useful for manufacturing the osmotic device are represented by a nontoxic member selected from the pharmaceutically acceptable group consisting essentially of a cellulose ester, cellulose diester, cellulose triester, cellulose ether, cellulose ester-ether, cellulose acylate, cellulose diacylate, cellulose triacylate, cellulose acetate, cellulose diacetate, cellulose triacetate, cellulose acetate propionate, and cellulose acetate butyrate. Suitable semipermeable polymers useful for manufacturing osmotic devices are disclosed in U.S. Pat. Nos. 3,845,770; 3,916,899; 4,008,719; 4,036,228, and 4,111,210. These patents are assigned to the ALZA Corporation of Palo Alto, Calif., the assignee of this patent application. In an embodiment, the wall of the osmotic device can be a laminate comprising a semipermeable lamina in laminar arrangement with a microporous lamina. The semipermeable lamina is formed from the above polymers. The microporous lamina has a plurality of micropores and interconnected micropaths for admitting external fluid into the device. The microporous lamina can comprise the above polymers containing a pore former that is dissolved, or leached from the lamina, when the osmotic device is in dispensing operation in the biological environment of use. The pore formers are non-toxic and they do not react with the materials forming the laminated wall. On their removal from the lamina, the paths formed fill with fluid, and these paths become a means for fluid to enter the device, acting in cooperation with the semipermeable lamina. Typical pore formers are represented by sodium chloride, potassium chloride, sorbitol, mannitol, polyethylene glycol, hydroxypropyl methylcellulose, and hydroxypropyl butylcellulose. Osmotic dispensing devices having a laminated wall comprising a semipermeable lamina and a microporous lamina are disclosed in U.S. Pat. No. 4,160,452, assigned to the ALZA Corporation. The osmotic device in another embodiment can be coated on its exterior surface with a nontoxic coating containing a non-toxic and water soluble dye. The coating can be on the semipermeable wall or it can be on the laminated wall. For example, the coating can comprise hydrooxypropyl methylcellulose mixed with Food, Drug and Cosmetic pharmaceutically acceptable yellow aluminum lake dye.

The expression passageway as used herein for an osmotic device includes an aperture, orifice, bore, hole and the like embracing osmotic dimensions through the wall. The expression also includes an erodible element in the wall, such as a gelatin plug that erodes and forms an osmotic passageway in the environment of use. A detailed description of osmotic passageways, and the maximum and minimum dimensions for osmotic passageways are disclosed in U.S. Pat. Nos. 3,845,770 and 3,916,899. These patents are assigned to the ALZA Corporation.

The amount of haloperidol in the osmotic device generally will vary depending on the therapeutic response sought in the biological environment. Generally the device will contain from 0.1 mg to 250 mg of haloperidol, with individual devices containing for example 0.5 mg, 2.0 mg, 3.0 mg, 10.0 mg, 100 mg, and the like. Generally, the osmotic device will contain from 0.3 mg to 750 mg of the di- or tricarboxylic acid, with individual devices containing 0.3 mg, 1.5 mg, 6.0 mg, 9.0 mg, 30.9 mg, 300 mg, and the like. The haloperidol and the carboxylic acid can be in the compartment of the osmotic device in various forms such as a dry, solid, granule, powder, pressed mass, film and the like. Also, the haloperidol and the carboxylic acid can be present in the compartment mixed with a binder, dye, lubricant, dispersant, and like pharmaceutical compounding ingredients. The drug haloperidol is well known to the dispensing art in *Pharmaceutical Science*, by Remington, 14th Ed., pg. 1108, 1970, published by the Mack Publishing Company, Easton, Penn.

The pharmaceutical compounding ingredients include binders such as poly(ethylene glycol), gelatin, agar, carboxycellulose, poly(vinyl alcohol), and poly(vinyl pyrrolidone). Typical lubricants include stearic acid, magnesium stearate, zinc stearate, aluminum stearate, halogenated vegetable oil and talc. The compartment can contain also a disintegrant to effect dissolution and solution forming of haloperidol and citric acid for enhancing controlled delivery from the osmotic device. Typical disintegrants include lightly cross-linked poly(vinyl pyrrolidone), corn starch, potato starch, Veegum ®, bentonite, and citrus pulp. The coloring agents include Food, Drug and Cosmetic approved non-toxic dyes such as blue number 1 in lactose. Optionally, the dye in the compartment and in the wall can be the same dye or a different dye. The amount of a binder, a lubricant or a disintegrant usually is about 0.1 mg to 20 mg respectively.

The osmotic devices provided by this invention containing haloperidol and the di- or tricarboxylic acid are manufactured by standard manufacturing techniques. For example, in one embodiment, the haloperidol is mixed with the carboxylic acid haloperidol solubility promoter, and with other compartment forming core ingredients by balling, calendering, stirring, and pressing the ingredients into a preselected shape corresponding to the shape of the final osmotic device. The material forming the wall of the device can be applied by dipping, molding, or spraying the pressed blend. One procedure for applying the semipermeable wall, or the laminated wall is the air suspension technique. The air suspension technique can be used for manufacturing a wall formed of a single layer, or formed of a multiplicity of layers. The air suspension procedure is described in U.S. Pat. No. 2,799,241; in *J. Am. Pharm. Assocc.*, Vol. 48, pgs. 451 to 459, 1959; and in ibid, Vol. 49, pages 82 to 84, 1960. An osmotic passageway is made by mechanical drilling, laser drilling, punching or cutting with a die. A procedure for forming the passageway using a laser is described in U.S. Pat. Nos. 3,916,899; and in 4,088,864, both assigned to the ALZA Corporation. The osmotic delivery device designed for oral administration can embrace various conventional shapes and sizes such as round with a diameter of 3/16 inches to 9/16 inches, or it can be shaped like a solid capsule having a range of sizes from triple zero to zero, and from 1 to 8. In these forms, the osmotic device is sized, shaped and adapted for administering haloperidol to warm-blooded animals, which term animals includes humans. Other standard manufacturing procedures are described in *Modern Plastic Encyclopedia*, Vol. 46, pgs. 62 to 70, 1969; in *Remington's Pharmaceutical Sciences*, 14th Ed., pgs. 1649 to 1698, 1980; and in *The Therapy and Practice of Industrial Pharmacy*, by Lackmann et al., pgs 197 to 225, 1970, published by Lea & Febiger Co., Philadelphia, Pa.

DESCRIPTION OF EXAMPLES OF THE INVENTION

The following examples are merely illustrative of the present invention and they should not be considered as limiting the scope of the invention in any way, as these examples and other equivalents thereof will become more apparent to those versed in the art in the light of the present disclosure, and the accompanying claims.

EXAMPLE 1

An osmotic therapeutic device for the controlled and continuous delivery of the beneficial drug haloperidol is made as follows: first, 28.35 g of haloperidol, 444.15 g of citric acid anhydrous, 10.00 g of polyvinyl pyrrolidone and 10.00 g of cross-linked Povidone are passed through a 60 mesh screen and mixed in a V-blender for 1 hour. Then, the blended ingredients are transferred to a larger blender and a granulating fluid consisting of ethanol:water 90:10 by volume is added to the blender and blended for 20 minutes. The homogenously blended ingredients next are passed through a 30 mesh screen and dried in a forced air oven for 16 hours at 50° C.

After drying, the granules are passed through a 20 mesh screen and 7.5 g of stearic acid is added to the granules. All the ingredients are blended for 15 minutes. The granules are transferred to a conventional Manesty tablet press and compressed into 176 mg, 8 mm concave reservoir forming core.

The haloperidol reservoirs are transferred to an Aeromatic ® air suspension coater, and a film consisting of cellulose acetate having an acetyl content of 39.8% is coated around the drug reservoirs. The semipermeable film is coated around the reservoir from a composition comprising 33 g of the cellulose acetate dissolved in a solvent consisting of 510 ml of methylene chloride and 105 ml of methanol. After the semipermeable film is formed around the reservoir, they are transferred to a forced air oven and dried for 48 hours at 50° C. Next, an osmotic passageway having a 0.36 mm diameter is laser drilled through the semipermeable wall. The semipermeable wall weighed 13.5 mg and it is 0.13 mm thick. The haloperidol citric acid ratio is 1:15.7.

Figure 1:
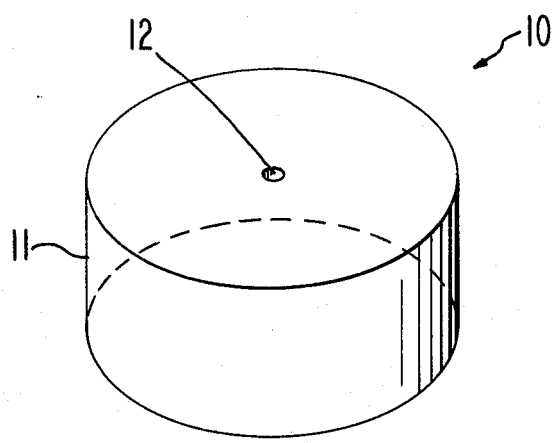
In FIG. 1, the osmotic device 10 is seen comprising a body 11 with a passageway 12 that connects the exterior with the interior of osmotic device 10.
Figure 2:
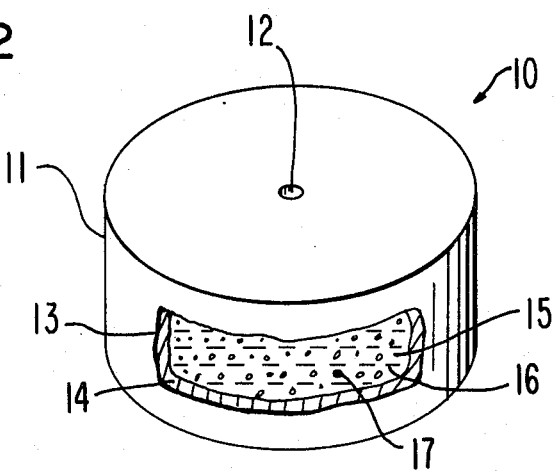
In FIG. 2, osmotic device 10 is seen in opened section at 13, and it comprises semipermeable wall 14 that surrounds and defines internal compartment 15. Compartment 15 contains haloperidol 16, citric acid 17 and the other dispensing ingredients.
Figure 4:
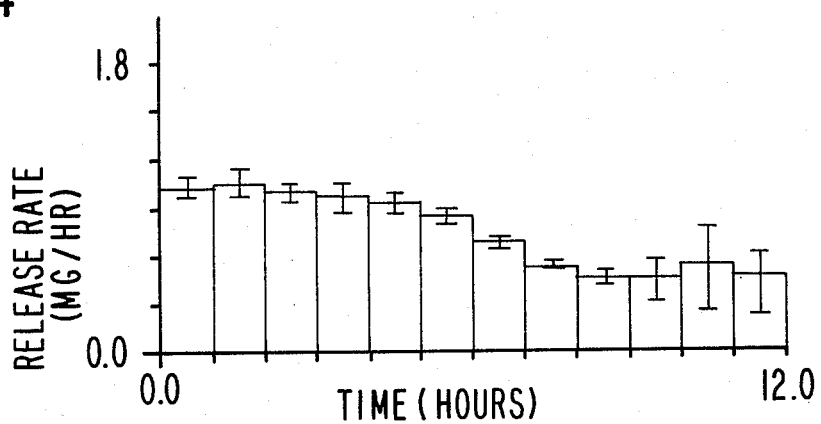
FIG. 4 depicts the release rate of haloperidol from the osmotic device.
Figure 5:
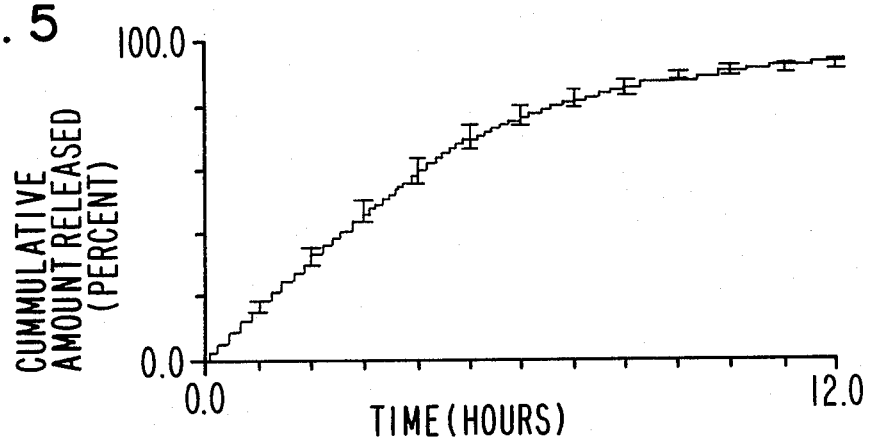
FIG. 5 depicts the cumulative amount of haloperidol delivered over a 12 hour delivery period.

The osmotic haloperidol therapeutic delivery devices prepared by the example are illustrated in FIGS. 1 and 2. In FIG. 1, the osmotic device 10 is seen comprising a body 11 with a passageway 12 that connects the exterior with the interior of osmotic device 10. In FIG. 2, osmotic device 10 is seen in opened section at 13, and it comprises semipermeable wall 14 that surrounds and defines internal compartment 15. Compartment 15 contains haloperidol 16, citric acid 17 and the other dispensing ingredients. FIG. 4 depicts the release rate of haloperidol from the osmotic device. In FIG. 4, the first 4 hours of release are measured in artificial gastric fluid, and the next 8 hours are measured in artificial intestional fluid. FIG. 5 depicts the cumulative amount of haloperidol delivered over a 12 hour delivery period.

EXAMPLE 2

An osmotic device that delivers haloperidol independent of the pH of the biological environment, is shaped, sized and manufactured for oral administration into the gastrointestinal tract as follows: first, 22.5 g of haloperidol, 450 g of anhydrous citric acid, 8.75 mg of non-cross-linked Povidone and 8.75 mg of cross-linked Povidone are mixed, passed through a 60 mesh stainless steel screen and blended for 1 hour at room temperature. Next, the blended ingredients are transferred to a larger blender and 40 ml of a granulating fluid consisting of ethanol:water 90:10 by volume is added to the blender, and the ingredients blended for 20 minutes. The thoroughly blended ingredients are passed next through a 30 mesh screen and dried in a forced air oven at 50° C. for 16 to 17 hours.

Then, the dried granules are passed through a 20 mesh screen and 10.0 mg of magnesium stearate is added to the granules. The ingredients are blended for 15 minutes, and the blended granules transferred to a conventional Manesty press. The ingredients are compressed into haloperidol reservoirs, each weighing 225 mg containing 10 mg of haloperidol and having a haloperidol citric acid ratio of 1 to 20. The compressed drug had a diameter of about 8.1 mm.

The haloperidol compartment forming compositions are transferred to an air suspension coater and surrounded with a semipermeable wall. The semipermeable wall is formed from a wall forming composition comprising 35 g of cellulose acetate having an acetyl content of 39.8 from an organic solvent consisting essentially of 550 ml of methylene chloride and 110 ml of methanol. After the semipermeable wall is formed surrounding the drug reservoir, they are dried in a forced air oven for 50 hours at 50° C. Next, a 0.4 mm passageway is laser drilled through the semipermeable wall connecting the interior compartment with the exterior of the osmotic device. Each osmotic device made according to the example weighed about 233.6 mg. The haloperidol drug reservoir weighed 225 mg and comprises 4.5% haloperidol, 90% citric acid, 1.75% non-cross-linked Povidone, 1.75% cross-linked Povidone and 2% magnesium stearate. The semipermeable wall weighed 8.6 mg. The osmotic device has an average rate of haloperidol release of about 0.83 mg over a 12 hour time span. The cumulative rate of release is depicted in FIG. 6. In the Figure, the bars represent the maximum and minimum rate of release for 6 measurements at the time of measurement.

EXAMPLE 3

The procedure of Example 2 is repeated with the manufacturing procedures as previously described, except that in this example, the drug reservoir weighed 44.9 mg consisting of 2 mg of haloperidol and the semipermeable cellulose acetate wall weighed 4.4 mg. The osmotic passageway is 0.35 mm, and the device delivers haloperidol for 12 hours.

EXAMPLE 4

The procedure of Example 2 is repeated with all previous conditions as described, except that in this example the starting batch comprises 10 g of haloperidol, 462.5 g of anhydrous citric acid, 8.75 g of noncross-linked Povidone, 8.75 g of cross-linked Povidone, and 10 g of magnesium stearate. The final osmotic device comprises a haloperidol drug reservoir weighing 100 mg containing 2 mg of haloperidol in a haloperidol to citric acid ratio of 1:46, and the semipermeable cellulose triacetate wall weighed 9.2 mg. The osmotic passageway measure 0.4 mm and the device delivers haloperidol for 12 hours.

EXAMPLE 5

The procedure of Example 2 is repeated with all previous conditions as described, except that in this example the haloperidol and citric acid are present in a 1 to 100 ratio. The final osmotic device has a 0.36 mm passageway, the compartment weighed 214 mg and consisted of 0.94% haloperidol, 93.6% citric acid, 1.75% noncross-linked Povidone, 1.75% cross-linked Povidone and 2% magnesium stearate. The semipermeable wall weighed 14 mg. The release rate in mg/hr for haloperidol is illustrated in FIG. 7.

EXAMPLE 6

An oral, osmotic device for the delivery of haloperidol to a patient in need thereof is manufactured as follows: a haloperidol drug composition is prepared for housing in the compartment of the osmotic device by thoroughly blending 15 mg of haloperidol base, 100 mg of maleic acid, 5 mg of gelatin, 3 mg of corn starch and 3 mg of stearic acid, and then compressing the homogenous blend into a precompartment forming drug formulation. Next, the compressed drug formulation is placed in an air suspension machine and coated with a microporous lamina forming composition. The microporous lamina composition comprises 49% weight of cellulose acetate having an acetyl content of 39.8%, 28.5% by weight of hydroxypropyl methylcellulose and 22.5% by weight of polyethylene glycol 4000. The lamina is formed from a methylene chloride—95% ethanol lamina solvent (80:20 wt:wt). The microporous lamina is 0.14 mm thick.

Figure 3:
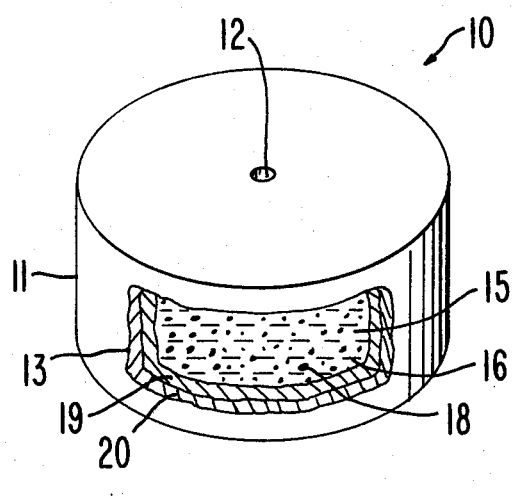
In FIG. 3, osmotic device 10 is seen in opened section at 13. Device 10 comprises body 11, passageway 12, internal compartment 15 containing haloperidol 16 and maleic acid 18. The laminated wall of device 10 comprises internal microporous lamina 19 in laminar arrangement with exterior semipermeable lamina 20. Next, a 0.4 mm passageway is laser drilled through the semipermeable wall connecting the interior compartment with the exterior of the osmotic device. The haloperidol drug reservoir weighed 225 mg amd comprises 4.5% haloperidol, 90% citric acid, 1.75% noncross-linked Povidone, 1.75% cross-linked Povidone and 2% magnesium stearate. The semipermeable wall weighed 8.6 mg. The osmotic device has an average rate of haloperidol release of abut 0.83 mg over a 12 hour time span.

Next, an exterior semipermeable lamina is laminated onto the microporous lamina in the conventional air suspension machine. The semipermeable lamina forming composition comprises 90% by weight of cellulose acetate having an acetyl content of 39.8% and 10% cellulose acetate having an acetyl content of 32%. The semipermeable lamina is applied in laminar arrangement from a solvent mixture comprising methylene chloride and 95% ethanol, 80:20 wt:wt. The osmotic devices are dried and a passageway having a 0.26 mm diameter is drilled with a laser through the laminated wall. The device in operation delivers haloperidol in the stomach and in the intestine for its tranquilizer effect. In FIG. 3, osmotic device 10 is seen in opened section at 13. Device 10 comprises body 11, passageway 12, internal compartment 15 containing haloperidol 16 and maleic acid 18. The laminated wall of device 10 comprises internal microporous lamina 19 in laminar arrangement with exterior semipermeable lamina 20.

EXAMPLE 7

An oral osmotic device for the controlled and continuous delivery of haloperidol is made by following the general procedure described above. In the osmotic device of this example, the comparment housed a drug formulation comprising 20 mg of haloperidol, 75 mg of malic acid, 4 mg of dextrose, 2 mg of potato starch and 3 mg of magnesium stearate. The formulation after compressing has a diameter of 9 mm. The device has a laminated wall comprising an interior semipermeable lamina consisting essentially of 60% by weight of cellulose acetate having an acetyl content of 43.5% and a degree of substitution of 3 and 40% by weight of cellulose acetate having an acetyl content of 39.8 and a degree of substitution of 2.4. The semipermeable lamina is applied from a solvent consisting essentially of methylene chloride and methanol, 80:20 by weight. The device has an exterior microporous lamina consisting essentially of 55% by weight of cellulose acetate having an acetyl content of 39.8%, 35% by weight of sorbitol, and 10% by weight of polyethylene glycol 400. The lamina is applied from a solvent comprising methylene chloride-methanol-water, 26:35:3 by weight. The semipermeable lamina is 0.12 mm thick, and the microporous lamina is 0.13 mm thick. The device has a 0.25 mm passageway.

EXAMPLE 8

An osmotic therapeutic device for the controlled and continuous delivery of haloperidol is made according to the procedure of Example 1, with all conditions as described except for the compartment which contains an excess of citric acid and succinic acid, in an amount of 400.15 g of citric acid to 44 g of succinic acid.

The invention in the presently preferred embodiments pertains to (1) a method for the management of psychotic disorders in a patient having such conditions; (2) a method for tranquilizing a patient in need of same; and (3) a method for treating hyperactivity in a human patient suffering from hyperactivity, which method in (1), (2) or (3) administers the beneficial drug haloperidol to the patient, wherein said method comprises the steps of: (A) admitting orally an osmotic device adapted, shaped and sized into the gastrointestional tract of the patient, the osmotic device comprising: (a) a wall formed of a nontoxic semipermeable composition that is permeable to the passage of an exterior fluid and substantially impermeable to the passage of haloperidol, the wall surrounding and forming; (b) a compartment containing a dosage unit amount of haloperidol and an effective amount of citric acid for increasing the solubility and delivery of haloperidol from the osmotic device; and (c) a passageway in the wall for communicating the exterior of the osmotic device with the interior of the osmotic device; (B) imbibing exterior fluid through the semipermeable wall into the compartment at a rate determined by the permeability of the semipermeable wall and the osmotic pressure gradient across the semipermeable wall to form a solution comprising haloperidol and citric acid that is hydrodynamically and osmotically delivered from the osmotic device; and (C) delivering haloperidol in a therpeutically effective amount through the passageway at a controlled rate and continuously to the gastrointestional tract of the patient to produce the desired beneficial effect over a prolonged period of time. The method of the invention also comprises an improvement wherein the compartment contains halodperidol and maleic acid, or haloperidol and malic acid, or haloperidol citric acid and succinic acid, and the beneficial drug is delivered at a controlled rate and continuously over a period of time from 15 minutes to 24 hours, in a therapeutically effective amount sufficient to produce the desired therapeutic effect to a warm-blooded animal in need thereof.

The invention provides an osmotic therapeutic system manufactured in the form of an osmotic device containing haloperidol, an improved method of haloperidol therapy. While there has been described and pointed out the novel features of the invention as applied to presently preferred embodiments, those skilled in the art will appreciate that various modifications, changes and omissions in the invention illustrated and described can be made without departing from the spirit of the invention.

We claim:

1. An osmotic system for the controlled delivery of haloperidol to an environment of use comprising:
    (a) a wall a semipermeable composition permeable to the passage of an exterior fluid, and substantially impermeable to the passage of haloperidol, the wall surrounding and forming:
    (b) a compartment comprising a dosage unit amount of haloperidol and an effective amount of citric acid for increasing the solubility of haloperidol thereby enhancing the delivery of haloperidol; and,
    (c) at least one passageway through the wall communicating the exterior of the system with the interior of the system for delivering haloperidol at a controlled rate over time.

2. The osmotic system for the controlled delivery of haloperidol to an environment of use according to claim 1, wherein the wall comprises a semipermeable composition comprising a member selected from the group consisting of a cellulose ester, cellulose diester, cellulose triester, celluose ether, cellulose acylate, cellulose diacylate, cellulose triacylate, and cellulose ester ether.

3. The osmotic system for the controlled delivery of haloperidol to an environment of use according to claim 1, wherein the compartment comprises a binder, lubricant and a disintegrating agent.

4. The osmotic system for the controlled delivery of haloperidol to an environment of use according to claim 1, wherein the compartment comprises a noncrosslinked polyvinyl pyrrolidone, cross-linked polyvinyl pyrrolidone, and stearic acid.

5. The osmotic system for the controlled delivery of haloperidol to an environment of use according to claim 1, wherein the semipermeable compositon comprises cellulose acetate.

6. The osmotic system for the controlled delivery of haloperidol to an environment of use according to claim 1, wherein the compartment comprises noncross-linked polyvinyl pyrrolidone, cross-linked polyvinyl pyrrolidone, and magnesium stearate.

7. An osmotic system for the controlled delivery of the drug haloperidol to an environment of use, comprising:
    (a) a wall comprising a nontoxic semipermeable polymeric composition permeable to the passage of an exterior fluid, and substantially impermeable to the package of drug, the wall surrounding and forming:
    (b) a compartment comprising haloperidol and maleic acid for increasing the solubility of haloperidol and thereby concomitantly increasing the amount of haloperidol delivered from system; and,
    (c) at least one passageway through the wall communicating the exterior of the system with the interior of the system for delivering haloperidol at a controlled rate over time.

8. The osmotic system for the controlled delivery of the drug haloperidol according to claim 7, wherein the environment of use is a human.

9. The osmotic system for the controlled delivery of the drug haloperidol according to claim 7, wherein the environment of use is a human and the system is sized and shaped for oral administration to the human.

10. An osmotic devide for the controlled delivery of a beneficial drug, comprising:
    (a) a wall comprising a nontoxic material permeable to the passage of an exterior fluid and substantially impermeable to the passage of drug, which wall surrounds and defines;
    (b) a compartment comprising a therapeutically effective amount of the beneficial drug haloperidol and an effective amount of maleic acid for increasing the solubility of haloperidol thereby increasing the amount of haloperidol delivered form the device; and,
    (c) at least one passageway through the wall connecting the exterior of the device with the compartment for delivering haloperidol from the device at a controlled rate over a prolonged period of time.

11. The osmotic device for the controlled delivery of the drug according to claim 10, wherein the device is adapted, sized and shaped for oral administration to a patient.

12. The osmotic device for the controlled delivery of the drug according to claim 11, wherein the malic acid increases the solubility of haloperidol in the presence of fluid imbibed through the wall into the compartment.

13. The osmotic device for the controlled delivery of the drug according to claim 11, wherein the malic acid increases the solubility of haloperidol in the presence of fluid imbibed through the wall into the compartment and concomitantly provides the controlled release of haloperidol over a prolonged period of time.

14. An osmotic system for the controlled delivery of the beneficial drug haloperidol to a biological environment of use, the osmotic system comprising:
   (a) a wall comprising a nontoxic semipermeable composition permeable to the passage of an exterior fluid present in the biological environment of use, and substantially impermeable to the passage of drug, which wall surrounds and forms;
   (b) a compartment;
   (c) a dosage unit amount of haloperidol in the compartment;
   (d) a composition for increasing the solubility of haloperidol in the presence of fluid imbibed from the biological environment into the compartment thereby enhancing the delivery of haloperidol from the compartment, the composition comprising succinic acid and at least one acid selected from the group consisting of citric, maleic and maleic acid; and,
   (e) at least one passageway through the wall connecting the exterior of the osmotic system with the compartment for delivering haloperidol at a controlled rate over time to the biological environment of use.

15. An osmotic system for the controled delivery of the drug haloperidol to a biological environment of use, the osmotic system comprising:
   (a) a wall comprising a nontoxic semipermeable composition permeable to the passage of a fluid present in the biological environment of use, and substantially impermeable to the passage of drug, which wall surrounds and forms;
   (b) a compartment;
   (c) a dosage amount of haloperidol in the compartment;
   (d) an acid selected form the group consisting of saturated and unsaturated dicarboxylic and tricarboxylic acid in the compartment for enhancing the solubility of haloperidol in the presence of fluid imbibed through the semipermeable wall into the compartment for enhancing the amount of haloperidol delivered from the compartment in unit time; and,
   (e) at least one passageway in the wall connecting the exterior of the osmotic system with the compartment for delivering a therapeutically effective amount of haloperidol to the environment of use at a controlled rate over a prolonged period of time.

* * * * *